United States Patent
Satchivi et al.

(10) Patent No.: US 9,788,542 B2
(45) Date of Patent: *Oct. 17, 2017

(54) SAFENED HERBICIDAL COMPOSITIONS INCLUDING 4-AMINO-3-CHLORO-5-FLUORO-6-(4-CHLORO-2-FLUORO-3-METHOXYPHENYL)PYRIDINE-2-CARBOX) ACID OR A DERIVATIVE THEREOF FOR USE IN CORN (MAIZE)

(71) Applicant: Dow AgroSciences LLC, Indianapolis, IN (US)

(72) Inventors: Norbert M. Satchivi, Carmel, IN (US); Hilde J. A. Eelen, Ghent (BE); Monte R. Weimer, Pittsboro, IN (US); Paul R. Schmitzer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/209,729

(22) Filed: Mar. 13, 2014

(65) Prior Publication Data
US 2014/0274704 A1 Sep. 18, 2014

Related U.S. Application Data

(60) Provisional application No. 61/792,777, filed on Mar. 15, 2013.

(51) Int. Cl.
*A01N 25/32* (2006.01)
*A01N 43/40* (2006.01)

(52) U.S. Cl.
CPC .................. *A01N 43/40* (2013.01)

(58) Field of Classification Search
None
See application file for complete search history.

(56) References Cited

U.S. PATENT DOCUMENTS

| | | | |
|---|---|---|---|
| 4,025,333 A | 5/1977 | Gulbenk | |
| 4,137,070 A * | 1/1979 | Pallos et al. | 504/112 |
| 5,484,760 A * | 1/1996 | Bussler et al. | 504/103 |
| 6,734,139 B1 * | 5/2004 | Feucht et al. | 504/128 |
| 7,314,849 B2 | 1/2008 | Balko et al. | |
| 8,652,999 B1 * | 2/2014 | Satchivi | A01N 43/40 504/130 |
| 8,791,048 B2 * | 7/2014 | Yerkes | A01N 43/40 504/100 |
| 8,796,177 B2 | 8/2014 | Mann et al. | |
| 8,809,232 B2 * | 8/2014 | Yerkes | A01N 43/40 504/100 |
| 8,841,233 B2 | 9/2014 | Yerkes et al. | |
| 8,841,234 B1 * | 9/2014 | Mann | A01N 43/40 504/100 |
| 8,846,570 B2 * | 9/2014 | Yerkes | A01N 43/40 504/100 |
| 8,871,680 B2 | 10/2014 | Yerkes et al. | |
| 8,871,681 B2 | 10/2014 | Mann et al. | |
| 8,883,682 B2 * | 11/2014 | Yerkes | A01N 43/40 504/129 |
| 8,889,591 B2 * | 11/2014 | Yerkes et al. | 504/100 |
| 8,895,470 B2 | 11/2014 | Yerkes et al. | |
| 8,901,035 B2 * | 12/2014 | Yerkes | A01N 43/40 504/100 |
| 8,906,825 B2 * | 12/2014 | Mann | A01N 43/40 504/100 |
| 8,906,826 B2 * | 12/2014 | Yerkes | A01N 43/40 504/100 |
| 8,912,120 B2 | 12/2014 | Yerkes et al. | |
| 8,912,121 B2 * | 12/2014 | Yerkes | A01N 43/40 504/100 |
| 8,912,123 B2 * | 12/2014 | Becker | A01N 43/40 504/105 |

(Continued)

FOREIGN PATENT DOCUMENTS

| | | |
|---|---|---|
| CL | 2015000184 | 4/2015 |
| CL | 2015000185 | 4/2015 |
| CL | 2015000186 | 4/2015 |
| CL | 2015000187 | 4/2015 |
| CL | 2015000188 | 4/2015 |
| CL | 2015000190 | 4/2015 |
| CL | 2015000182 | 7/2016 |
| CL | 2015002497 | 7/2016 |
| WO | 2012164013 A1 | 12/2012 |
| WO | 2014018358 A1 | 1/2014 |

*Primary Examiner* — Alton Pryor
(74) *Attorney, Agent, or Firm* — Michael J. Terapane; Meunier Carlin & Curfman, LLC

(57) ABSTRACT

A safened herbicidal composition for use in corn (maize) including a herbicidally effective amount of (a) a compound of formula (I):

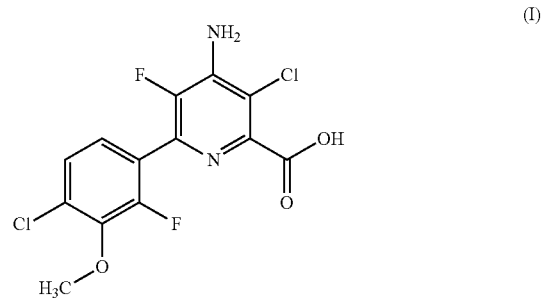

or an agriculturally acceptable salt or ester thereof and (b) a safener or a compatible herbicide capable of safening such as AD67, benzenesulfonamide, benoxacor, N-(aminocarbonyl)-2-chlorobenzenesulfonamide (2-CBSU), daimuron, dichlormid, dichloroacetamide, dicyclonon, fenchlorazole-ethyl, fenclorim, fluxofenim, furilazole, isoxadifen-ethyl, mefenpyr-diethyl, naphthopyranone, naphthalic anhydride (NA), oxabetrinil, oxime, phenylpyrimidine, phenylurea, a chemical from the quinolinyloxyacetate family of chemicals, or agriculturally acceptable salts, esters, or mixtures thereof. Methods for using the safened herbicidal composition for controlling undesirable vegetation in corn (maize) also are described.

17 Claims, No Drawings

(56) References Cited

U.S. PATENT DOCUMENTS

| | | | |
|---|---|---|---|
| 8,916,499 B2* | 12/2014 | Yerkes | A01N 43/40 504/100 |
| 9,237,747 B2* | 1/2016 | Yerkes | A01N 43/30 |
| 2010/0137137 A1 | 6/2010 | Rosinger et al. | |
| 2013/0310256 A1 | 11/2013 | Yerkes et al. | |

* cited by examiner

SAFENED HERBICIDAL COMPOSITIONS INCLUDING 4-AMINO-3-CHLORO-5-FLUORO-6-(4-CHLORO-2-FLUORO-3-METHOXYPHENYL)PYRIDINE-2-CARBOX) ACID OR A DERIVATIVE THEREOF FOR USE IN CORN (MAIZE)

CROSS REFERENCE TO RELATED APPLICATIONS

This application claims the benefit of U.S. Provisional Patent Application Ser. No. 61/792,777 filed Mar. 15, 2013, the disclosure of which is expressly incorporated herein by reference.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. Occasionally, however, such herbicides can injure the crop being protected in addition to the weeds and other vegetation intended to be controlled.

SUMMARY

Provided herein are safened herbicidal compositions for use in corn (maize) comprising a herbicidally effective amount of (a) a compound of the formula (I)

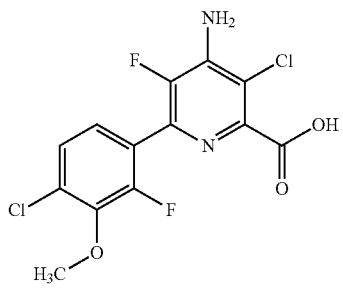

(I)

or an agriculturally acceptable salt or ester of thereof and (b) a safener or a compatible herbicide capable of safening such as AD67, benzenesulfonamide, benoxacor, N-(aminocarbonyl)-2-chlorobenzenesulfonamide (2-CBSU), daimuron, dichlormid, dichloroacetamide, dicyclonon, fenchlorazole-ethyl, fenclorim, fluxofenim, furilazole, isoxadifen-ethyl, mefenpyr-diethyl, naphthopyranone, naphthalic anhydride (NA), oxabetrinil, oxime, phenylpyrimidine, phenylurea, a chemical from the quinolinyloxyacetate family of chemicals, or agriculturally acceptable salts, esters, or mixtures thereof. The compositions may also contain an agriculturally acceptable adjuvant or carrier.

Provided herein also are methods of controlling undesirable vegetation in corn (maize) comprising applying to the corn (maize), contacting the vegetation, or area adjacent thereto a safened herbicidal composition comprising a herbicidally effective amount of (a) a compound of the formula (I)

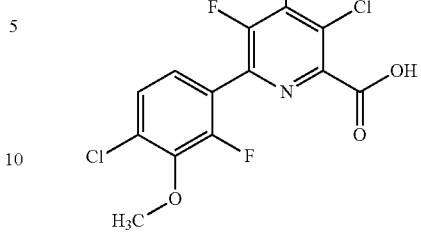

(I)

or an agriculturally acceptable salt or ester thereof and (b) a safener or a compatible herbicide capable of safening such as AD67, benzenesulfonamide, benoxacor, N-(aminocarbonyl)-2-chlorobenzenesulfonamide (2-CBSU), daimuron, dichlormid, dichloroacetamide, dicyclonon, fenchlorazole-ethyl, fenclorim, fluxofenim, furilazole, isoxadifen-ethyl, mefenpyr-diethyl, naphthopyranone, naphthalic anhydride (NA), oxabetrinil, oxime, phenylpyrimidine, phenylurea, a chemical from the quinolinyloxyacetate family of chemicals, or agriculturally acceptable salts, esters, or mixtures thereof.

DETAILED DESCRIPTION

Definitions

As used herein, the compound of formula (I) has the following structure:

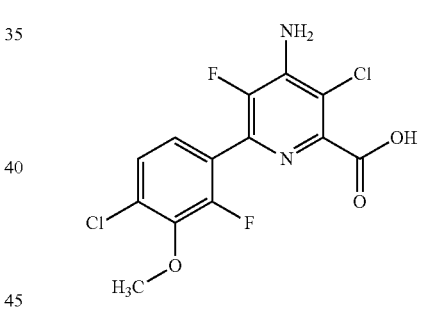

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

As used herein, safeners include AD67, benzenesulfonamide, benoxacor, N-(aminocarbonyl)-2-chlorobenzenesulfonamide (2-CBSU), daimuron, dichlormid, dichloroacetamide, dicyclonon, fenchlorazole-ethyl, fenclorim, fluxofenim, furilazole, isoxadifen-ethyl, mefenpyr-diethyl, naphthopyranone, naphthalic anhydride (NA), oxabetrinil, oxime, phenylpyrimidine, phenylurea, a chemical from the quinolinyloxyacetate family of chemicals, or agriculturally acceptable salts, esters, or mixtures thereof.

Chemicals from the quinolinyloxyacetate family of chemicals are described in U.S. Pat. No. 4,902,340. Chemicals/safeners from the quinolinyloxyacetate family of chemicals include derivatives of cloquintocet, such as cloquintocet acid, cloquintocet mexyl, cloquintocet triisopropylamine, and cloquintocet dimethylamine. Cloquintocet is the common name for (5-chloroquinolin-8-yloxy)acetic acid. Cloquintocet's safening activity is described in Tomlin, C. D. S., Ed. *The Pesticide Manual: A World Compendium,* 15*th* ed.; BCPC: Alton, 2009 (hereafter "*The Pesticide Manual,* Fifteenth Edition, 2009").

AD67 (MON 4660) is the common name for 4-(dichloroacetyl)-1-oxa-4-azaspiro[4,5]decane. AD67's safening activity is described in *The Pesticide Manual,* Thirteenth Edition, 2003.

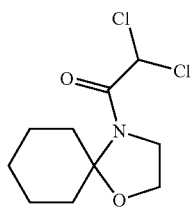

Benoxacor is the common name for (±)-4-(dichloroacetyl)-3,4-dihydro-3-methyl-2H-1,4-benzoxazine. Benoxacor's safening activity is described in *The Pesticide Manual,* Fifteenth Edition, 2009.

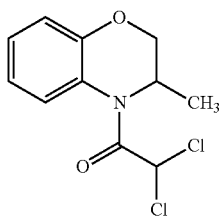 [SMILES: CC1COc2ccccc2N1C(=O)C(Cl)Cl]

2-CBSU is the common name for N-(aminocarbonyl)-2-chlorobenzenesulfonamide. 2-CBSU's safening activity is described in *Modern Crop Protection Compounds,* 2007.

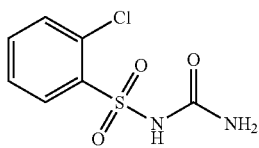 [SMILES: NC(=O)NS(=O)(=O)c1ccccc1Cl]

Daimuron is the common name for N-(4-methylphenyl)-N'-(1-methyl-1-phenylethyl)-urea. Its herbicidal activity is described in *The Pesticide Manual,* Fifteenth Edition, 2009.

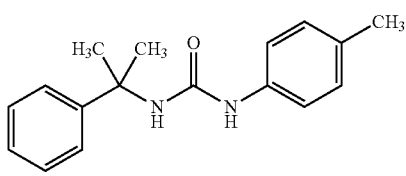 [SMILES: Cc1ccc(NC(=O)NC(C)(C)c2ccccc2)cc1]

Dichlormid is the common name for N,N-diallyl-2,2-dichloroacetamide. Its safening activity is described in *The Pesticide Manual,* Fifteenth Edition, 2009.

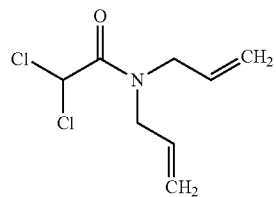

Dicyclonon (BAS 145 138H) is the common name for (RS)-1-dichloroacetyl-3,3,8a-trimethylperhydropyrrolo[1,2-c]pyrimidin-6(2H)-one. Its safening activity is described in *Pesticide Biochemistry and Physiology* 1992, 42, 128-139.

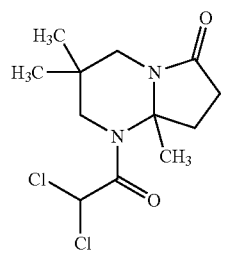 [SMILES: CC1(C)CN2C(=O)CCC2(C)N(C(=O)C(Cl)Cl)C1]

Fenchlorazole is the common name for 1-(2,4-dichlorophenyl)-5-(trichloromethyl)-1H-1,2,4-triazole-3-carboxylic acid. Its safening activity is described in *The Pesticide Manual,* Fifteenth Edition, 2009.

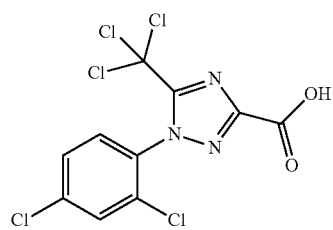 [SMILES: O=C(O)c1nc(C(Cl)(Cl)Cl)n(-c2ccc(Cl)cc2Cl)n1]

Fenclorim is the common name for 4,6-dichloro-2-phenylpyrimidine. Its safening activity is described in *The Pesticide Manual,* Fifteenth Edition, 2009.

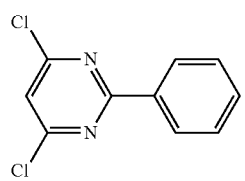 [SMILES: Clc1cc(Cl)nc(-c2ccccc2)n1]

Isoxadifen-ethyl is the common name for ethyl 4,5-dihydro-5,5-diphenyl-3-isoxazole-carboxylate. Its safening activity is described in *The Pesticide Manual,* Fourteenth Edition, 2006.

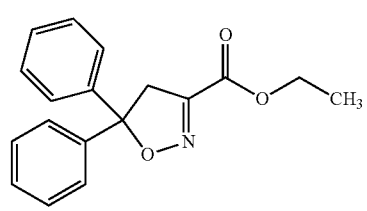 [SMILES: CCOC(=O)C1=NOC(c2ccccc2)(c2ccccc2)C1]

Fluxofenim is the common name for 1-(4-chlorophenyl)-2,2,2-trifluoroethanone O-(1,3-dioxolan-2-ylmethyl)oxime. Its safening activity is described in *The Pesticide Manual*, Fifteenth Edition, 2009.

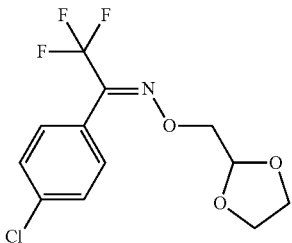 [SMILES: FC(F)(F)/C(=N/OCC1OCCO1)c1ccc(Cl)cc1]

Furilazole is the common name for (±)-3-(dichloroacetyl)-5-(2-furanyl)-2,2-dimethyloxazolidine. Its safening activity is described in *The Pesticide Manual*, Fifteenth Edition, 2009.

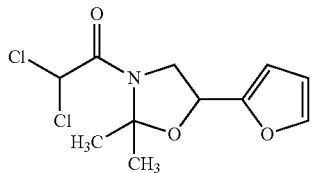

Mefenpyr-diethyl is the common name for 1-(2,4-dichlorophenyl)-4,5-dihydro-5-methyl-1H-pyrazole-3,5-dicarboxylic acid. Its safening activity is described in *The Pesticide Manual*, Fifteenth Edition, 2009.

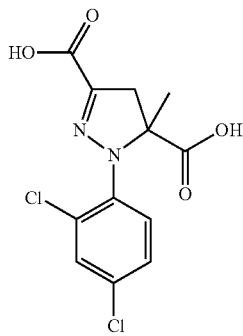 [SMILES: CC1(C(=O)O)CC(C(=O)O)=NN1c1ccc(Cl)cc1Cl]

Naphthalic anhydride is the common name for naphthalene-1,8-dicarboxylic anhydride. Its safening activity is described in *The Pesticide Manual*, Eighth Edition, 1987.

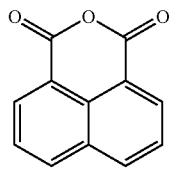

Oxabetrinil is the common name for α-[(1,3-dioxolan-2-yl)methoxyimino]benzeneacetonitrile. Its safening activity is described in *The Pesticide Manual*, Fifteenth Edition, 2009.

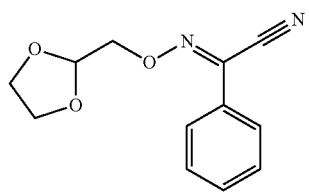 [SMILES: N#C/C(=N/OCC1OCCO1)c1ccccc1]

As used herein, herbicide means an active ingredient that kills, controls, or otherwise adversely modifies the growth of plants.

As used herein, a herbicidally effective or vegetation controlling amount is an amount of active ingredient which causes an adversely modifying effect and includes deviations from natural development, killing, regulation, desiccation, retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, and established vegetation.

As used herein, a safener is a compound that selectively protects crop plants, in this case corn (maize), from herbicide damage without significantly reducing activity in target weed species.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending upon the pH, may be in the dissociated or undissociated form. Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are safened herbicidal compositions for use in corn (maize) comprising a herbicidally effective amount of (a) a compound of the formula (I)

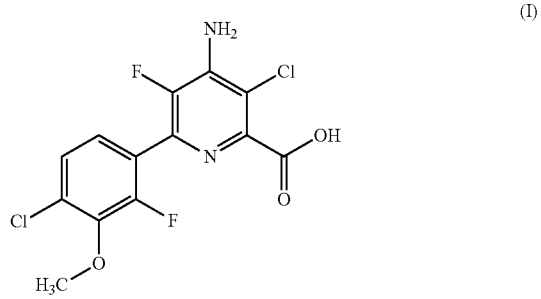 [SMILES: COc1c(Cl)ccc(-c2nc(C(=O)O)c(Cl)c(N)c2F)c1F]

or an agriculturally acceptable salt or ester of thereof and (b) a safener or a compatible herbicide capable of safening. Safeners or compatible herbicides capable of safening useful with the compositions and methods described herein include, but are not limited to AD-67 (MON 4660), benzenesulfonamide, benoxacor, N-(aminocarbonyl)-2-chlorobenzenesulfonamide (2-CBSU), daimuron, dichlormid, dichloroacetamide, dicyclonon, fenchlorazole-ethyl, fenclorim, fluxofenim, furilazole, isoxadifen-ethyl, mefenpyr-diethyl, naphthopyranone, naphthalic anhydride (NA), oxabetrinil, oxime, phenylpyrimidine, phenylurea, a chemical from the quinolinyloxyacetate family of chemicals, or agriculturally acceptable salts, esters, or mixtures thereof.

Provided herein are also methods of controlling undesirable vegetation in corn (maize) comprising applying to the corn (maize), contacting the vegetation, or applying to the soil or water adjacent thereto with a safened herbicidal composition including a herbicidally effective amount of (a) the compound of formula (I) or an agriculturally acceptable salt or ester thereof and (b) a safener or a compatible herbicide capable of safening including, but not limited to, AD-67 (MON 4660), benzenesulfonamide, benoxacor, N-(aminocarbonyl)-2-chlorobenzenesulfonamide (2-CBSU), daimuron, dichlormid, dichloroacetamide, dicyclonon, fenchlorazole-ethyl, fenclorim, fluxofenim, furilazole, isoxadifen-ethyl, mefenpyr-diethyl, naphthopyranone, naphthalic anhydride (NA), oxabetrinil, oxime, phenylpyrimidine, phenylurea, a chemical from the quinolinyloxyacetate family of chemicals, or agriculturally acceptable salts, esters, or mixtures thereof.

Corn (maize) plants to be protected from the adverse effect of undesirable plant growth may be damaged to a certain degree when an effective dose of herbicide is used. Safening as used herein means preventing the adverse effect of a herbicide on the corn (maize) plant, i.e., protecting the corn (maize) plant without, at the same time, noticeably influencing (i.e., overly diminishing) the herbicidal action on the undesirable plant growth, i.e., weeds, to be combated.

The compound of the formula (I) or an agriculturally acceptable salt or ester of thereof and (b) a safener or a compatible herbicide capable of safening described herein can be applied either separately or together as part of a system. When part of a system, for example, the compound of the formula (I) or an agriculturally acceptable salt or ester of thereof and (b) a safener or a compatible herbicide capable of safening described herein can be formulated in one composition, tank-mixed, applied simultaneously, or applied sequentially. The compound of the formula (I) or an agriculturally acceptable salt or ester of thereof and (b) a safener or a compatible herbicide capable of safening described herein can be applied pre-emergently to the corn (maize) or the undesirable vegetation or post-emergently to the corn (maize) or the undesirable vegetation. Further, the compound of the formula (I) or an agriculturally acceptable salt or ester of thereof can be applied pre-emergently or post-emergently to the corn (maize) or the undesirable vegetation and b) a safener or a compatible herbicide capable of safening described herein can be applied as a seed treatment to the corn (maize).

Herbicidal activity is exhibited by the compounds of formula (I) when they are applied directly to a plant or to the area adjacent the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. The compositions of formula (I) described herein can be applied as a post-emergence application, or pre-emergence application, to relatively immature undesirable vegetation to achieve the maximum control of weeds.

The compositions and methods provided herein can be used to control weeds in corn (maize) crops, and also in glyphosate-tolerant, 5-enolpyruvylshikimate-3-phosphate (EPSP) synthase inhibitor-tolerant, glufosinate-tolerant, glutamine synthetase inhibitor-tolerant, dicamba-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, phenoxy auxin-tolerant, pyridyloxy auxin-tolerant, auxin-tolerant, auxin transport inhibitor-tolerant, aryloxyphenoxypropionate-tolerant, acetyl CoA carboxylase (ACCase) inhibitor-tolerant, acetolactate synthase (ALS) or acetohydroxy acid synthase (AHAS) inhibitor-tolerant, 4-hydroxyphenyl-pyruvate dioxygenase (HPPD) inhibitor-tolerant, phytoene desaturase inhibitor-tolerant, carotenoid biosynthesis inhibitor-tolerant, protoporphyrinogen oxidase (PPO) inhibitor-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant and bromoxynil-tolerant corn (maize) crops. The compositions and methods provided herein can be used with corn (maize) seeds, applied to nursery corn (maize), as seed treatments, pre-plant treatments and post-emergence treatments to corn (maize). The compositions and methods may be used in controlling undesirable vegetation in corn (maize) genetically transformed to express specialized traits. Examples of specialized traits include agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture). Additional examples include those expressing proteins toxic to invertebrate pests, such as *Bacillus thuringiensis* or other insecticidal toxins, or those with "stacked" foreign genes expressing insecticidal toxins, herbicide resistance, nutrition-enhancement and/or other beneficial traits.

The compositions and methods provided herein can be used to control undesirable vegetation in corn (maize) For example, the combination of (a) compound of formula (I) or agriculturally acceptable ester or salt thereof and (b) a safener or a compatible herbicide capable of safening including, but not limited to, benzenesulfonamide, benoxacor, N-(aminocarbonyl)-2-chlorobenzenesulfonamide (2-CBSU), daimuron, dichlormid, dichloroacetamide, dicyclonon, fenchlorazole-ethyl, fenclorim, fluxofenim, furilazole, isoxadifen-ethyl, mefenpyr-diethyl, naphthopyranone, naphthalic anhydride (NA), oxabetrinil, oxime, phenylpyrimidine, phenylurea, a chemical from the quinolinyloxyacetate family of chemicals, or agriculturally acceptable salts, esters, or mixtures thereof, is used to control undesirable vegetation in corn (maize).

For example, the compositions and methods provided herein can be used to control undesirable vegetation including, but not limited to, undesirable vegetation of the weed genera such as *Abutilon theophrasti* Medik. (velvetleaf, ABUTH), *Amaranthus retroflexus* L. (redroot pigweed, AMARE), *Amaranthus* species (pigweeds and amaranths, AMASS), *Ambrosia artemisiifolia* L. (common ragweed, AMBEL), *Ambrosia trifida* L. (giant ragweed, AMBTR), *Chenopodium album* L. (common lambsquarters, CHEAL), *Commelina benghalensis* L. (tropical spiderwort, COMBE), *Daucus carona* L. (wild carrot, DAUCA), *Euphorbia heterophylla* L. (wild poinsettia, EPHHL), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Galium aparine* L. (catchweed bedstraw, GALAP), *Helianthus annuus* L. (common sunflower, HELAN), *Lamium purpureum* L. (purple deadnettle, LAMPU), *Sida* species (sida, SIDSS), *Sida spinosa* L. (prickly sida, SIDSP), *Sinapis* species (SINSS), *Sinapis arvensis* L. (wild mustard, SINAR), *Stellaria media* (L.) Vill. (common chickweed, STEME), *Solanum nigrum* L. (black nightshade, SOLNI), or *Xanthium strumarium* L. (common cocklebur, XANST).

In some embodiments, the methods provided herein are utilized to control undesirable vegetation in corn (maize). In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Brassica* species (BRSSS), *Cirsium arvense* (L.) Scop. (Canada thistle, CIRAR), *Kochia scoparia* (L.) Schrad. (kochia, KCHSC), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Veronica persica* Poir. (Persian speedwell, VERPE), *Viola arvensis* Murr. (field violet, VIOAR), or *Viola tricolor* L. (wild violet, VIOTR), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or*Urochloa plantaginea* (Link) R. D. Webster (alexandergrass, BRAPL), *Cenchrus echinatus* L. (southern sandbur, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Ambrosia psilostachya* DC. (western ragweed, AMBPS), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacoce latifolia* (broadleaved buttonweed, BOILF), *Cirsium arvense* (L.) Scop. (Canada thistle, CIRAR), *Datura stramonium* L. (jimsonweed, DATST), *Euphorbia hirta* L. or *Chamaesyce hirta* (L.) Millsp. (garden spurge, EPHHI), *Euphorbia dentata* Michx. (toothed spurge, EPHDE), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Solanum ptychanthum* Dunal (eastern black nightshade, SOLPT), or *Tridax procumbens* L. (coat buttons, TRQPR).

In the compounds and methods described herein, an agriculturally acceptable ester or salt of compound (I) is employed. An agriculturally acceptable ester, such as an aralkyl or alkyl ester, can be employed. The ester can be a $C_1$-$C_4$ alkyl ester, an n-butyl ester, a benzyl ester, or a substituted benzyl ester. Additionally, the carboxylic acid form of compound (I) or the carboxylate salt of the compound of formula (I) can be used.

In the compositions and methods described herein, the compound of formula (I) or salt or ester thereof is used in combination with a safener or a compatible herbicide capable of safening. The weight ratio of the compound of formula (I) or salt or ester thereof to the safener or a compatible herbicide capable of safening is within the range of from 1:100 to 25:1. The weight ratio of the compound of formula (I) or salt or ester thereof to the safener or a compatible herbicide capable of safening also can be within the range from 1:90 to 25:1, 1:80 to 25:1, 1:70 to 25:1, 1:60 to 25:1, 1:50 to 25:1, 1:40 to 25:1, 1:30 to 25:1, 1:20 to 25:1, 1:18 to 25:1, 1:16 to 25:1, 1:14 to 25:1, 1:12 to 25:1, 1:10 to 25:1, 1:8 to 25:1, 1:6 to 25:1, 1:5 to 25:1, 1:4 to 25:1, 1:3 to 25:1, 1:2 to 25:1, 1:1 to 25:1, 1:100 to 20:1, 1:100 to 18:1, 1:100 to 16:1, 1:100 to 14:1, 1:100 to 12:1, 1:100 to 10:1, 1:100 to 9:1, 1:100 to 8:1, 1:100 to 7:1, 1:100 to 6:1, 1:100 to 5:1, 1:100 to 4:1, 1:100 to 3:1, 1:100 to 2:1, 1:100 to 1:1, 1:50 to 20:1, 1:40 to 20:1, 1:30 to 20:1, 1:25 to 15:1, 1:20 to 15:1, 1:18 to 12:1, 1:16 to 10:1, 1:14 to 10:1, 1:12 to 10:1, 1:10 to 1:1, 1:9 to 1:1, 1:8 to 1:1, 1:7 to 1:1, 1:6 to 1:1, 1:5 to 1:1, 1:4 to 1:1, 1:3 to 1:1, or 1:2 to 1:1. Additionally, the weight ratio of the compound of formula (I) or salt or ester thereof to the safener or a compatible herbicide capable of safening can be 25:1, 20:1, 18:1, 16:1, 14:1, 12:1, 10:1, 9:1, 8:1, 7:1, 6:1, 5:1, 4:1, 3:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:6, 1:7, 1:8, 1:9, 1:10, 1:11, 1:12, 1:13, 1:14, 1:15, 1:16, 1:18, 1:20, 1:25, 1:50, 1:75, or 1:100.

The application rate will depend upon the particular type of weed to be controlled, the degree of control required, and the timing and method of application. In the compositions described herein the compound of formula (I) or salt or ester thereof can be applied at an application rate of from 1 gram active ingredient per hectare (g ai/ha) to 200 g ai/ha based on the total amount of the compound of formula (I) or salt or ester thereof in the composition. Additionally, in the compositions described herein the compound of formula (I) or salt or ester thereof can be applied at an application rate of from 1 g ai/ha to 175 g ai/ha, 5 g ai/ha to 150 g ai/ha, 1 g ai/ha to 100 g ai/ha, 5 g ai/ha to 200 g ai/ha, 10 g ai/ha to 200 g ai/ha, 12.5 g ai/ha to 150 g ai/ha, 12.5 g ai/ha to 200 g ai/ha, 1 g ai/ha to 150 g ai/ha, 2 g ai/ha to 100 g ai/ha, 2 g ai/ha to 75 g ai/ha, 2 g ai/ha to 50 g ai/ha, 2 g ai/ha to 35 g ai/ha, or 5 g ai/ha to 35 g ai/ha based on the total amount of the compound of formula (I) or salt or ester thereof in the composition. In the compositions described herein the safener or a compatible herbicide capable of safening can be applied at an application rate of from 1 g ai/ha to 1200 g ai/ha. Additionally, in the compositions described herein the safener or a compatible herbicide capable of safening can be applied at an application rate of from 1 g ai/ha to 600 g ai/ha, 1 g ai/ha to 500 g ai/ha, 1 g ai/ha to 400 g ai/ha, 1 g ai/ha to 300 g ai/ha, 1 g ai/ha to 200 g ai/ha, 1 g ai/ha to 100 g ai/ha, 1 g ai/ha to 50 g ai/ha, 1 g ai/ha to 10 g ai/ha, 1 g ai/ha to 4 g ai/ha, 4 g ai/ha to 1200 g ai/ha, 4 g ai/ha to 600 g ai/ha, 5 g ai/ha to 600 g ai/ha, 6 g ai/ha to 500 g ai/ha, 7 g ai/ha to 400 g ai/ha, 5 g ai/ha to 300 g ai/ha, 4 g ai/ha to 200 g ai/ha, 10 g ai/ha to 150 g ai/ha, 12 g ai/ha to 100 g ai/ha, 5 g ai/ha to 1200 g ai/ha, 10 g ai/ha to 600 g ai/ha, 10 g ai/ha to 500 g ai/ha, 10 g ai/ha to 400 g ai/ha, 10 g ai/ha to 300 g ai/ha, or 10 g ai/ha to 200 g ai/ha based on the total amount of the safener or a compatible herbicide capable of safening in the composition. For example, the safener or a compatible herbicide capable of safening can be applied at a rate from 1 g ai/ha to 1200 g ai/ha and the compound of formula (I) or salt or ester thereof is applied at a rate from 1 g ae/ha to 200 g ae/ha.

The components of the mixtures described herein can be applied either separately or as part of a multipart herbicidal system.

The safened herbicide mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+ isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate salts and esters, halauxifen, halauxifen-methyl, glufosinate-ammonium, glufosinate-P-ammonium, glyphosate salts and esters, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, triallate, triasulfuron, triaziflam, tribenuron, tribenuronmethyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac, tritosulfuron, vernolate, xylachlor and salts, esters, optically active isomers and mixtures thereof.

The safened compositions and methods for their use described herein, can, further, be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAStolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes-of-action via single and/or multiple resistance mechanisms. The compound of formula (I) or salt or ester thereof and complementary herbicide or salt or ester thereof can be used in combination with herbicides that are selective for the crop being treated and which complement the spectrum of weeds controlled by these compounds at the application rate employed. The compositions described herein and other complementary herbicides can be applied at the same time, either as a combination formulation or as a tank-mix.

The compositions and methods may be used in controlling undesirable vegetation in corn (maize) possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, pentachlorophenol, thidiazuron, tribufos, aviglycine, ethephon, maleic hydrazide, gibberellins, gibberellic acid, abscisic acid, ancymidol, fosamine, glyphosine, isopyrimol, jasmonic acid, maleic hydrazide, mepiquat, 2,3,5-triiodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol, and trinexapac. In some embodiments, the plant growth regulator is mixed with the compound of formula (I) to cause a preferentially advantageous effect on plants.

The compositions provided herein can further include one or more agriculturally acceptable adjuvant or carrier. Suitable adjuvants or carriers should not be phytotoxic to corn (maize), particularly at the concentrations employed in applying the compositions for selective weed control in the presence of corn (maize), and should not react chemically with herbicidal components or other composition ingredients. Such mixtures can be designed for application directly to weeds or their locus or can be concentrates or formulations that are normally diluted with additional carriers and adjuvants before application. The adjuvants or carriers can be solids, such as, for example, dusts, granules, water-dispersible granules, or wettable powders, or liquids, such as, for example, emulsifiable concentrates, solutions, emulsions or suspensions. Additionally, the adjuvants or carriers can also be provided as a pre-mix or tank-mixed.

Suitable agricultural adjuvants and carriers are well known to those of skill in the art and include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Examples of liquid carriers that can be used in the compositions and methods described herein include water and organic solvents. Examples of useful organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is useful as a carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

The compositions described herein may further include one or more surface-active agents. Such surface-active agents can be used in both solid and liquid compositions, and can be designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in *McCutcheon's Detergents and Emulsifiers Annual*, MC Publishing Corp.: Ridgewood, N.J., 1998 and in *Encyclopedia of Surfactants*, Vol. I-III, Chemical Publishing Co.: New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters. These materials, such as vegetable or seed oils and their esters, can be used interchangeably as an agricultural adjuvant, as a liquid carrier or as a surface active agent.

Other additives useful in the compositions provided herein include, but are not limited to, compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of active ingredients in the compositions described herein is generally from 0.0005 to 98 percent by weight. Additionally, concentrations from 0.0006 to 90 percent by weight can be used. In compositions designed to be employed as concentrates, the active ingredients can be present in a concentration from 0.1 to 98 weight percent or from 0.5 to 90 weight percent. Such compositions can be diluted with an inert carrier, such as, for example, water, before application. The diluted compositions usually applied to vegetation or the soil or water adjacent thereto can contain from 0.0006 to 15.0 weight percent active ingredient or from 0.001 to 10.0 weight percent.

The present compositions can be applied to vegetation or the soil or water adjacent thereto by the use of conventional ground or aerial dusters, sprayers, and granule applicators, by addition to irrigation or paddy water, and by other conventional means known to those skilled in the art.

The following Examples are presented to illustrate various aspects of the compositions and methods described herein and should not be construed as limitations to the claims.

EXAMPLES

Example I

Evaluation of Postemergence Herbicidal Safening in Corn (Maize)

Seeds of the desired test plant species were planted in Sun Gro MetroMix 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of ester (benzyl) compound of formula (I) (Compound A benzyl ester) and various safeners alone and in combination. Compound of formula (I) and safener components were applied on active ingredient basis.

For treatments comprised of formulated compounds, measured amounts of compound of formula (I) were placed individually in 25 mL glass vials and diluted in a volume of 1.25% volume per volume (v/v) Agri-dex crop oil concentrate to obtain stock solutions. If a test compound did not dissolve readily, the mixture was warmed and/or sonicated. Stock solutions of the formulated safeners were prepared following the same procedure. Application solutions were prepared by mixing the required amount of each stock solution and addition of an appropriate volume of an aqueous mixture of 1.25% v/v of Agri-dex crop oil concentrate to the appropriate final concentrations of application solutions.

For treatments comprised of formulated compound of formula (I) and technical compound of safeners, weighed amounts of the technical materials were placed individually in 25 mL glass vials and dissolved in a volume of 97:3 v/v acetone/DMSO to obtain stock solutions at the highest safener concentration, and measured amounts of the formulated compound of formula (I) was placed individually in 25 mL glass vials and diluted in a volume of 1.25% (v/v) Agri-dex crop oil concentrate to obtain stock solutions at the highest concentration. If a test compound did not dissolve readily, the mixture was warmed and/or sonicated. Application solutions were prepared by adding an appropriate amount of each stock solution and diluted to the appropriate final concentrations with the addition of an appropriate volume of an aqueous mixture of 1.25% (v/v) Agri-dex crop oil concentrate.

Application solutions were applied to the plant material with an overhead Mandel track sprayer equipped with 8002E nozzles calibrated to deliver 187 liters per hectare (L/ha) over an application area of 0.503 square meters ($m^2$) at a spray height of 18 inches (43 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture;

B=observed efficacy of active ingredient B at the same concentration as used in the mixture.

Some of the compounds tested, application rates employed, plant species tested, and results are given in Table 1 through Table 13.

TABLE 1

CORN (ZEAMX) SAFENING FROM POSTEMERGENCE APPLICATIONS OF COMPOUND A BENZYL ESTER AND SAFENER ISOXADIFEN-ETHYL

| Application Rate (g ai/ha) | | ZEAMX | |
|---|---|---|---|
| Compound A | Isoxadifen-ethyl | Obs | Exp |
| 4 | 0 | 10 | — |
| 6 | 0 | 16 | — |
| 20 | 0 | 32 | — |
| 40 | 0 | 45 | — |
| 0 | 4 | 0 | — |
| 0 | 8 | 0 | — |
| 0 | 6 | 0 | — |
| 0 | 12 | 0 | — |
| 0 | 20 | 0 | — |
| 0 | 40 | 0 | — |
| 0 | 80 | 0 | — |
| 0 | 160 | 3 | — |
| 4 | 4 | 0 | 10 |
| 4 | 8 | 0 | 10 |
| 6 | 6 | 0 | 16 |
| 6 | 12 | 0 | 16 |
| 20 | 20 | 2 | 32 |
| 20 | 40 | 3 | 32 |
| 20 | 80 | 5 | 32 |
| 40 | 40 | 2 | 45 |
| 40 | 80 | 2 | 45 |
| 40 | 160 | 2 | 47 |

ZEAMX = *Zea mays* L.
g ai/ha = grams active ingredient per hectare
Obs = observed
Exp = expected

TABLE 2

CORN (ZEAMX) SAFENING FROM POSTEMERGENCE APPLICATIONS OF COMPOUND A BENZYL ESTER AND SAFENER CLOQUINTOCET-MEXYL

| Application Rate (g ai/ha) | | ZEAMX | |
|---|---|---|---|
| Compound A | Cloquintocet-mexyl | Obs | Exp |
| 20 | 0 | 32 | — |
| 40 | 0 | 45 | — |
| 0 | 20 | 0 | — |
| 0 | 40 | 0 | — |
| 0 | 80 | 0 | — |
| 0 | 160 | 0 | — |
| 20 | 20 | 8 | 32 |
| 20 | 40 | 3 | 32 |
| 20 | 80 | 0 | 32 |
| 40 | 40 | 5 | 45 |
| 40 | 80 | 8 | 45 |
| 40 | 160 | 5 | 45 |

ZEAMX = *Zea mays* L.
g ai/ha = grams active ingredient per hectare
Obs = observed
Exp = expected

TABLE 3

CORN (ZEAMX) SAFENING FROM POSTEMERGENCE APPLICATIONS OF COMPOUND A BENZYL ESTER AND SAFENER BENOXACOR

| Application Rate (g ai/ha) | | ZEAMX | | HELAN | | ABUTH | |
|---|---|---|---|---|---|---|---|
| Compound A | Benoxacor | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 3 | 23 | 97 | 94 | 95 | 95 |
| 40 | 5 | 18 | 23 | 95 | 94 | 97 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 4

CORN (ZEAMX) SAFENING FROM POSTEMERGENCE APPLICATIONS OF COMPOUND A BENZYL ESTER AND SAFENER 2-CBSU

| Application Rate (g ai/ha) | | ZEAMX | | HELAN | | ABUTH | |
|---|---|---|---|---|---|---|---|
| Compound A | 2-CBSU | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 18 | 23 | 95 | 94 | 97 | 95 |
| 40 | 5 | 40 | 23 | 96 | 94 | 96 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 5

CORN (ZEAMX) SAFENING FROM POSTEMERGENCE APPLICATIONS OF COMPOUND A BENZYL ESTER AND SAFENER DAIMURON

| Application Rate (g ai/ha) | | ZEAMX | | HELAN | | ABUTH | |
|---|---|---|---|---|---|---|---|
| Compound A | Daimuron | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 10 | 23 | 97 | 94 | 97 | 95 |
| 40 | 5 | 30 | 23 | 96 | 94 | 97 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 6

CORN (ZEAMX) SAFENING FROM POSTEMERGENCE APPLICATIONS OF COMPOUND A BENZYL ESTER AND SAFENER DICHLORMID

| Application Rate (g ai/ha) | | ZEAMX | | HELAN | | ABUTH | |
|---|---|---|---|---|---|---|---|
| Compound A | Dichlormid | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 8 | 23 | 97 | 94 | 97 | 95 |
| 40 | 5 | 20 | 23 | 96 | 94 | 97 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 7

CORN (ZEAMX) SAFENING FROM POSTEMERGENCE APPLICATIONS OF COMPOUND A BENZYL ESTER AND SAFENER DICYCLONON

| Application Rate (g ai/ha) | | ZEAMX | | HELAN | | ABUTH | |
|---|---|---|---|---|---|---|---|
| Compound A | Dicyclonon | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 8 | 23 | 95 | 94 | 97 | 95 |
| 40 | 5 | 30 | 23 | 94 | 94 | 97 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 8

CORN SAFENING FROM POSTEMERGENCE APPLICATIONS OF COMPOUND A BENZYL ESTER AND SAFENER FLUXOFENIM

| Application Rate (g ai/ha) | | ZEAMX | | HELAN | | ABUTH | |
|---|---|---|---|---|---|---|---|
| Compound A | Fluxofenim | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 18 | 23 | 96 | 94 | 97 | 95 |
| 40 | 5 | 30 | 23 | 94 | 94 | 97 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 9

CORN (ZEAMX) SAFENING FROM POSTEMERGENCE APPLICATIONS OF COMPOUND A BENZYL ESTER AND SAFENER FURILAZOLE

| Application Rate (g ai/ha) | | ZEAMX | | HELAN | | ABUTH | |
|---|---|---|---|---|---|---|---|
| Compound A | Furilazole | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 8 | 23 | 93 | 94 | 97 | 95 |
| 40 | 5 | 25 | 23 | 93 | 94 | 97 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 10

CORN (ZEAMX) SAFENING FROM POSTEMERGENCE APPLICATIONS OF COMPOUND A BENZYL ESTER AND SAFENER ISOXADIFEN-ETHYL

| Application Rate (g ai/ha) | | ZEAMX | | HELAN | | ABUTH | |
|---|---|---|---|---|---|---|---|
| Compound A | Isoxadifen-ethyl | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 0 | 23 | 93 | 94 | 97 | 95 |
| 40 | 5 | 8 | 23 | 95 | 94 | 96 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 11

CORN (ZEAMX) SAFENING FROM POSTEMERGENCE APPLICATIONS OF COMPOUND A BENZYL ESTER AND SAFENER MEFENPYR-DIETHYL

| Application Rate (g ai/ha) | | ZEAMX | | HELAN | | ABUTH | |
|---|---|---|---|---|---|---|---|
| Compound A | Mefenpyr | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 8 | 23 | 94 | 94 | 97 | 95 |
| 40 | 5 | 28 | 23 | 93 | 94 | 96 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 12

CORN (ZEAMX) SAFENING FROM POSTEMERGENCE APPLICATIONS OF COMPOUND A BENZYL ESTER AND SAFENER NAPHTHALIC ANHYDRIDE

Application Rate (g ai/ha)

| | Naphthalic | ZEAMX | | HELAN | | ABUTH | |
|---|---|---|---|---|---|---|---|
| Compound A | anhydride | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 13 | 23 | 93 | 94 | 97 | 95 |
| 40 | 5 | 40 | 23 | 93 | 94 | 99 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected

TABLE 13

CORN (ZEAMX) SAFENING FROM POSTEMERGENCE APPLICATIONS OF COMPOUND A BENZYL ESTER AND SAFENER OXABETRINIL

| Application Rate (g ai/ha) | | ZEAM | | HELAN | | ABUTH | |
|---|---|---|---|---|---|---|---|
| Compound A | Oxabetrinil | Obs | Exp | Obs | Exp | Obs | Exp |
| 40 | 0 | 23 | — | 94 | — | 95 | — |
| 0 | 40 | 0 | — | 0 | — | 0 | — |
| 0 | 5 | 0 | — | 0 | — | 0 | — |
| 40 | 40 | 15 | 23 | 97 | 94 | 97 | 95 |
| 40 | 5 | 35 | 23 | 93 | 94 | 97 | 95 |

ZEAMX = *Zea mays* L.
HELAN = *Helianthus annuus* L.
ABUTH = *Abutilon theophrasti* Medik.
g ai/ha = grams active ingredient per hectare
Obs = observed
Exp = expected The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or method steps may be explicitly mentioned herein; however, other combinations of components and method steps are included, even though not explicitly stated. The term comprising and variations thereof as used herein is used synonymously with the term including and variations thereof and are open, non-limiting terms.

What is claimed is:

1. A safened herbicidal composition for use in corn comprising a herbicidally effective amount of (a) the benzyl ester of the compound of the formula (I)

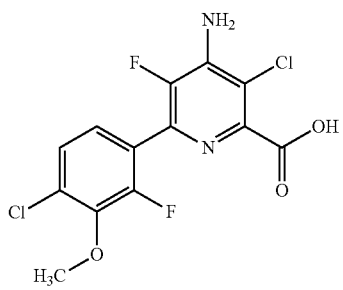

(I)

and (b) a safener; wherein said (b) reduces injury by said (a).

2. The composition of claim 1, wherein (b) is selected from the group consisting of isoxadifen-ethyl, cloquintocet-mexyl, benoxacor, 2-CBSU, daimurom, dichlormid, dicyclonon, fluxofenim, flurilazole, mefenpyr-diethyl, naphthalic anhydride, and oxabetrinil.

3. The composition of claim 1, wherein said (b) comprises isoxadifen-ethyl, and a ratio of the (a) to (b) is from 8:1 to 1:8.

4. The composition of claim 1, wherein said (b) comprises cloquintocet-mexyl, and a ratio of the (a) to (b) is from 1:1 to 1:4.

5. The composition of claim 1, wherein said (b) comprises benoxacor, 2-CB SU, daimurom, dichlormid, dicyclonon, fluxofenim, flurilazole, mefenpyr-diethyl, naphthalic anhydride, or oxabetrinil, and a ratio of the (a) to (b) is from 1:1 to 8:1.

6. A method for controlling the undesirable vegetation in the corn comprising applying to the corn, contacting the vegetation, or area adjacent thereto the composition of claim 1.

7. A method for controlling undesirable vegetation in corn comprising applying to the corn, contacting the undesirable vegetation, or area adjacent thereto a safened herbicidal composition comprising a herbicidally effective amount of (a) the benzyl ester of the compound of the formula (I)

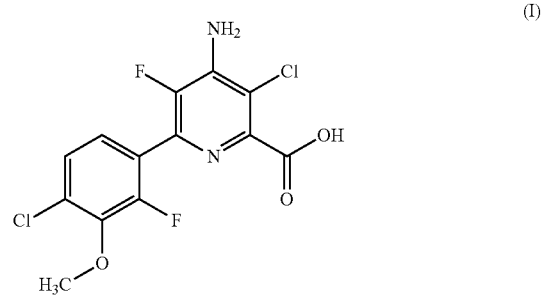 [SMILES: COc1c(Cl)ccc(-c2nc(C(=O)O)c(Cl)c(N)c2F)c1F]

(I)

and (b) a safener; wherein said (b) reduces injury by said (a).

8. The method of claim 7, wherein the undesirable vegetation is immature.

9. The method of claim 7, wherein the (a) and (b) are applied pre-emergently to the corn or the undesirable vegetation.

10. The method of claim 7, wherein the (a) and (b) are applied post-emergently to the corn or the undesirable vegetation.

11. The method of claim 7, wherein the (a) is applied pre-emergently or post-emergently to the corn or the undesirable vegetation and the b) is applied as a seed treatment to the corn.

12. The method of claim 7, wherein said (b) is selected from the group consisting of isoxadifen-ethyl, cloquintocet-mexyl, benoxacor, 2-CBSU, daimurom, dichlormid, dicyclonon, fluxofenim, flurilazole, mefenpyr-diethyl, naphthalic anhydride, and oxabetrinil.

13. The method of claim 7, wherein said (b) comprises isoxadifen-ethyl, and a ratio of the (a) to (b) is from 8:1 to 1:8.

14. The method of claim 7, wherein said (b) comprises cloquintocet-mexyl, and a ratio of the (a) to (b) is from 1:1 to 1:4.

15. The method of claim 7, wherein said (b) comprises benoxacor, 2-CB SU, daimurom, dichlormid, dicyclonon, fluxofenim, flurilazole, mefenpyr-diethyl, naphthalic anhydride, or oxabetrinil, and a ratio of the (a) to (b) is from 1:1 to 8:1.

16. The method of claim 7, wherein the safened herbicidal composition further comprises an agriculturally acceptable adjuvant or carrier.

17. The method of claim 7, wherein the corn is glyphosate tolerant, glufosinate tolerant, dicamba tolerant, phenoxy auxin tolerant, pyridyloxy auxin tolerant, aryloxyphenoxypropionate tolerant, acetyl CoA carboxylase (ACCase) inhibitor tolerant, imidazolinone tolerant, acetolactate synthase (ALS) inhibitor tolerant, 4-hydroxyphenyl-pyruvate dioxygenase (HPPD) inhibitor tolerant, protoporphyrinogen oxidase (PPO) inhibitor tolerant, triazine tolerant, or bromoxynil tolerant.

* * * * *